(12) United States Patent
Shao et al.

(10) Patent No.: US 9,457,181 B2
(45) Date of Patent: Oct. 4, 2016

(54) CARDIAC LEAD WELDING

(71) Applicant: Cardiac Pacemakers, Inc., St. Paul, MN (US)

(72) Inventors: Haiping Shao, Plymouth, MN (US); Kenneth L. Gunter, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 115 days.

(21) Appl. No.: 14/254,341

(22) Filed: Apr. 16, 2014

(65) Prior Publication Data

US 2014/0223735 A1 Aug. 14, 2014

Related U.S. Application Data

(62) Division of application No. 12/846,587, filed on Jul. 29, 2010, now abandoned.

(60) Provisional application No. 61/243,637, filed on Sep. 18, 2009.

(51) Int. Cl.
*A61N 1/00* (2006.01)
*A61N 1/05* (2006.01)
*H01R 13/33* (2006.01)

(52) U.S. Cl.
CPC ............ *A61N 1/0573* (2013.01); *H01R 13/33* (2013.01); *H01R 2201/12* (2013.01); *Y10T 29/49002* (2015.01); *Y10T 29/49208* (2015.01); *Y10T 29/49213* (2015.01)

(58) Field of Classification Search
CPC ............ A61N 1/00; A61N 1/02; A61N 1/08; A61N 1/372; A61N 1/375; H01B 13/0009; H01B 13/0023; H01B 13/0026; H01B 13/2633; H01B 13/264; H01B 13/2646; H01B 13/2653
See application file for complete search history.

(56) References Cited

U.S. PATENT DOCUMENTS

| | | | |
|---|---|---|---|
| 5,569,883 | A | 10/1996 | Walter et al. |
| 5,575,814 | A | 11/1996 | Giele et al. |
| 6,717,100 | B2 | 4/2004 | Ruben |
| 2004/0167442 | A1 | 8/2004 | Shireman et al. |
| 2006/0037461 | A1 | 2/2006 | Yasumura |
| 2009/0210044 | A1 | 8/2009 | Reddy et al. |
| 2010/0305672 | A1 | 12/2010 | Felling et al. |
| 2010/0331940 | A1 | 12/2010 | Indravudh et al. |
| 2011/0071610 | A1 | 3/2011 | Shao et al. |

*Primary Examiner* — Christopher D Koharski
*Assistant Examiner* — Elizabeth K So
(74) *Attorney, Agent, or Firm* — Faegre Baker Daniels LLP

(57) ABSTRACT

An implantable lead may have a distal assembly including a coupler, a terminal pin and a conductive member rotatably secured to both the coupler and the terminal pin. The conductive member may be a fine-wire, multiple-filar coil. The conductive member may be welded to the coupler and/or the terminal pin by welding through banded portions formed within the distal and proximal ends, respectively, of the conductive member.

15 Claims, 9 Drawing Sheets

CARDIAC LEAD WELDING

CROSS-REFERENCE TO RELATED APPLICATIONS

This application is a divisional application of U.S. patent application Ser. No. 12/846,587, filed Jul. 29, 2010, entitled "CARDIAC LEAD WELDING" which claims priority under 35 U.S.C. §119(e) to U.S. Provisional Patent Application No. 61/243,637, filed on Sep. 18, 2009, entitled "CARDIAC LEAD WELDING," which is incorporated herein by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Example 1 is an implantable lead having a flexible body extending between a proximal end and a distal end. A connector assembly is secured to the proximal end for coupling the lead to an implantable medical device while a distal assembly is coupled to the distal end. The connector assembly includes a terminal pin that is rotatable relative to the body. A conductor member is rotatably disposed longitudinally within the body and is coupled to the terminal pin. The conductor member includes a multiple filar coil having a distal region, a proximal region and a banded portion that is formed within the distal region of the multiple filar coil. The distal assembly includes a housing having a distal region and a proximal region. The proximal region of the housing is fixedly coupled to the distal end of the body. A coupler having a proximal end and a distal end is rotatably disposed within the housing. A helical electrode is fixedly secured to the distal end of the coupler and the banded portion of the conductor member is fixedly secured to the proximal end of the coupler. The terminal pin is rotatably engaged with the coupler via the conductor member such that rotation of the terminal pin causes the coupler and the helical electrode to rotate and therefore translate relative to the housing.

In Example 2, the implantable lead of Example 1 in which the banded portion of the conductive member is welded to the proximal end of the coupler.

In Example 3, the implantable lead of Example 1 or Example 2 in which the banded portion extends radially at least substantially around the distal end of the conductive member.

In Example 4, the implantable lead of any of Examples 1-3 in which the banded portion includes two or more distinct banded regions within the distal end of the conductive member.

In Example 5, the implantable lead of Example 4 in which the banded portion of the conductive member is secured to the proximal end of the coupler by welding through at least one of the two or more distinct banded regions.

In Example 6, the implantable lead of any of Examples 1-5 in which the conductive member further includes a second banded portion formed within the proximal region of the conductive member.

In Example 7, the implantable lead of Example 6 in which the second banded portion of the conductive member is welded to the terminal pin.

Example 8 is a method of assembling an extendable/retractable active fixation lead having a coupler and a conductive member secured to the coupler, the conductive member having a distal region and a proximal region. The coupler includes a proximal portion configured to accommodate the distal region of the conductive member. The distal region of the conductive member is subjected to heat and pressure to form a banded portion. The banded portion is disposed about the proximal end of the coupler. The banded portion of the conductive member is welded to the coupler.

In Example 9, the method of Example 8 in which subjecting the distal region of the conductive member to heat and pressure includes subjecting the distal region of the conductive member to laser energy while applying an axial compressive force.

In Example 10, the method of Example 8 or Example 9 in which the conductive member includes a multiple filar coil.

In Example 11, the method of any of Examples 8-10 in which subjecting the distal region of the conductive member to heat and pressure includes banding together a plurality of adjacent filars.

In Example 12, the method of claim 11 in which welding the banded portion to the metal structure includes welding through the plurality of adjacent filars banded together.

In Example 13, the lead further including a terminal pin, the method of any of Examples 8-12, further including melting and compressing the proximal region of the conductive member, re-solidifying the proximal region of the conductive member to form a second banded portion, disposing the second banded portion about the terminal pin, and welding the second banded portion to the terminal pin.

In Example 14, the method of any of Examples 8-13, further including attaching a fixation helix to the coupler to form an assembly and disposing the assembly within a lead body.

Example 15 is a method of assembling an implantable lead that includes a coupler, terminal pin and a conductive member that extends between the coupler and the terminal pin. The conductive member is a multiple filar coil having a distal region and a proximal region. The distal region of the multiple filar coil is melted and compressed, and then re-solidified to form a banded portion. The banded portion is disposed proximate the coupler and is welded to the coupler. The proximal region of the multiple filar coil is melted and compressed, and then re-solidified to form a second banded portion. The second banded portion is disposed proximate the terminal pin and is welded to the terminal pin.

In Example 16, the method of Example 15 in the coupler includes a shaft portion configured to fit within the distal region of the multiple filar coil, and the method further includes fitting the distal region of the multiple filar coil over the shaft portion prior to welding the banded portion to the coupler.

In Example 17, the method of Example 15 in which the coupler is configured to accommodate the distal region of the multiple filar coil within the coupler, and the method further includes fitting the distal region of the multiple filar coil within the coupler prior to welding the coupler to the banded portion.

In Example 18, the method of any of Examples 15-17 in which the terminal pin is configured to extend within the proximal region of the multiple filar coil, and the method further includes fitting the proximal region of the multiple filar coil over the terminal pin prior to welding the banded portion to the terminal pin.

In Example 19, the method of any of Examples 15-17 in which the terminal pin is configured to accommodate the proximal region of the multiple filar coil within the terminal pin, and the method further includes fitting the proximal region of the multiple filar coil within the terminal pin prior to welding the terminal pin to the banded portion.

In Example 20, the method of any of Examples 15-19, further including the coupler and attached conductive member within a lead body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
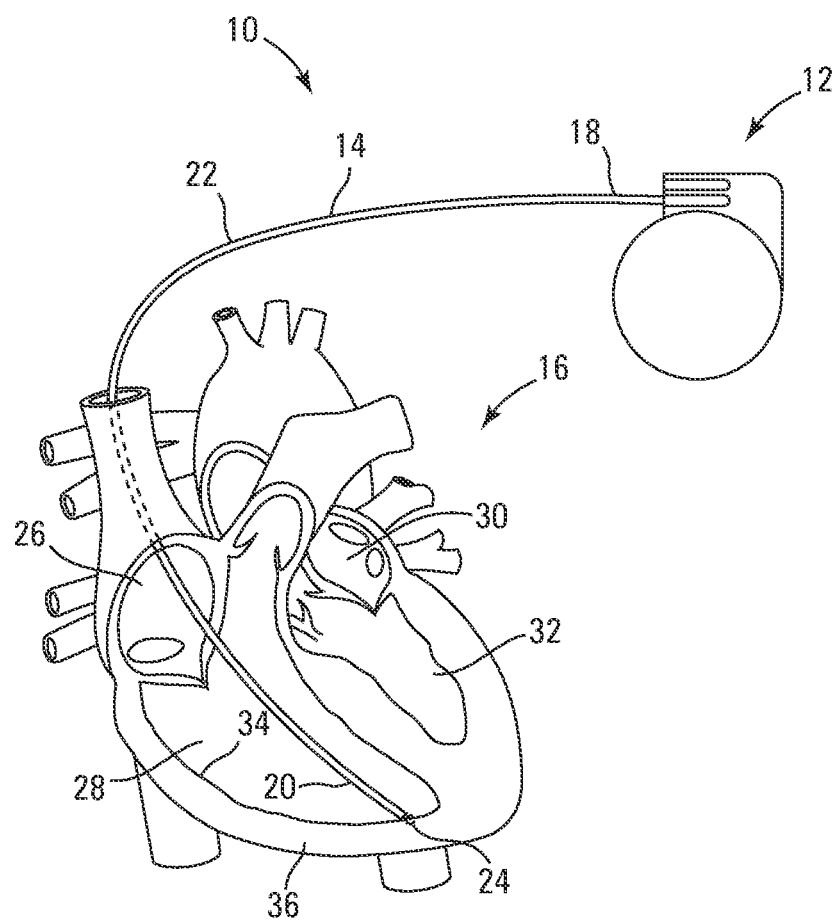
FIG. 1 is a combined cutaway and perspective view of an implantable medical device and lead in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes a fixation helix 24, which as will be discussed in greater detail below, locates and/or secures the distal region 20 within the heart 16. In the illustrated embodiment, the cardiac lead 14 is an active fixation lead. In some embodiments, the cardiac lead 14 may be a passive fixation lead, and thus may not include the fixation helix 24.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus can be used to sense the electrical activity of the heart 16 or to apply a stimulating pulse to the right ventricle 28. In other embodiments, the fixation helix 24 is not electrically active. Rather, in some embodiments, other components of the lead 14 are electrically active.

Figure 2:
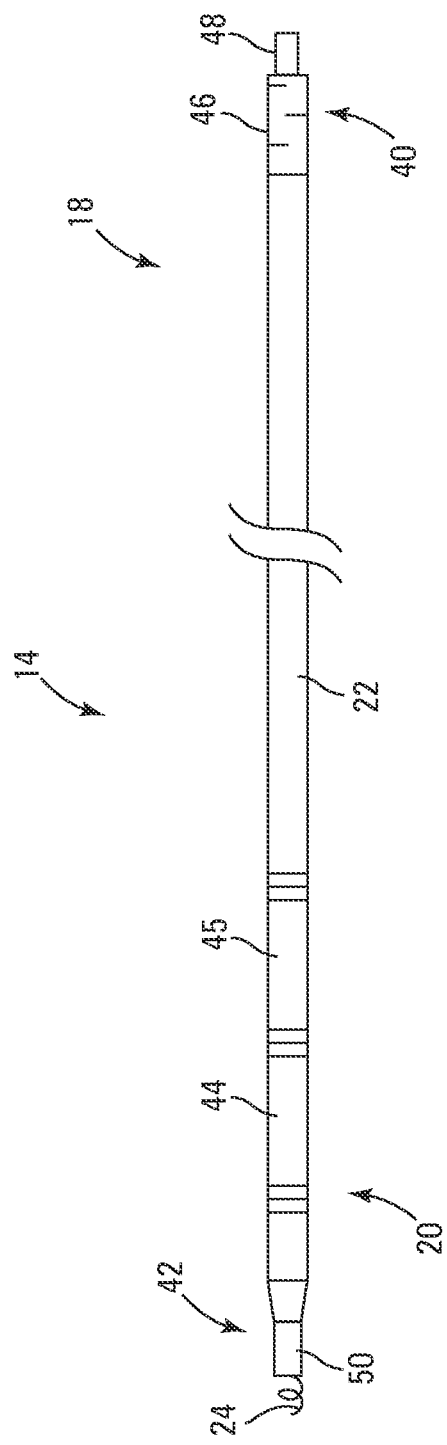
FIG. 2 is a side elevation view of the lead of FIG. 1.

FIG. 2 is an isometric illustration of the lead 14. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally through the lead body 22 such that rotating the terminal pin 48 (relative to the lead body 22) causes the conductor member to rotate within the lead body 22. In some embodiments, the terminal pin 48 includes an aperture extending therethrough in order to accommodate a guide wire or an insertion stylet.

The distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 may accommodate or include a structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a pace/sense electrode. In some embodiments, the fixation helix 24 is made of an electrically conductive material such as Elgiloy, MP35N, nickel, tungsten, tantalum, iridium, platinum, titanium, palladium, stainless steel as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

Figure 3:
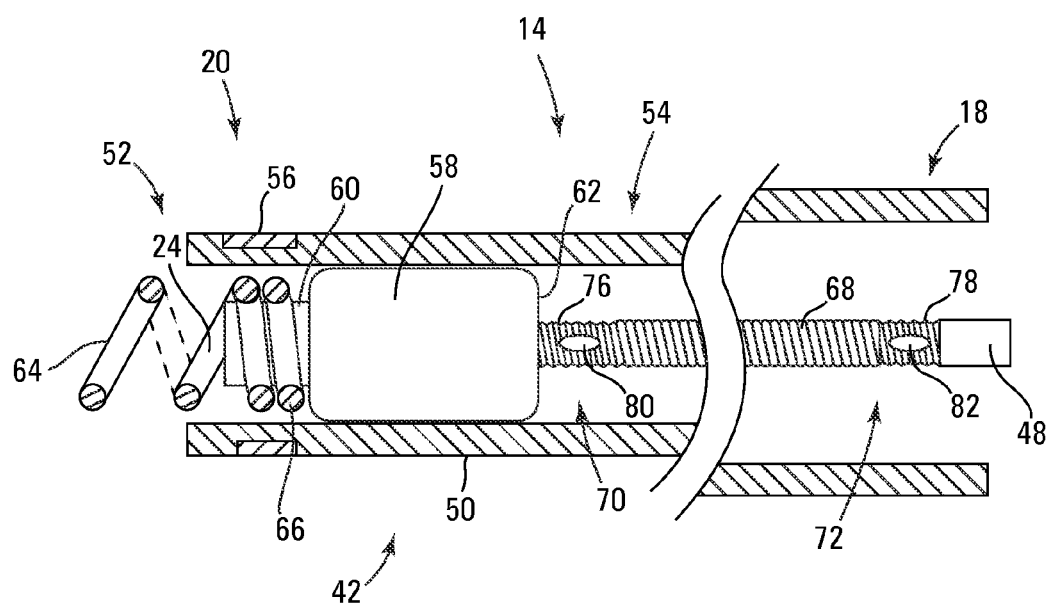
FIG. 3 is a cross-sectional view of the lead of FIG. 1.

FIG. 3 is a cross-sectional view of the lead 14. As shown in FIG. 3, the housing 50 includes a distal region 52 and a proximal region 54. The housing 50 is, in general, relatively rigid or semi-rigid. In some embodiments, the housing 50 is made of an electrically conductive material such as Elgiloy, MP35N, nickel, tungsten, tantalum, iridium, platinum, titanium, palladium, stainless steel as well as alloys of any of these materials. In some embodiments, the housing 50 is made of a non-electrically conductive material such as PES, polyurethane-based thermoplastics, ceramics, polypropylene and PEEK.

In the illustrated embodiment, a drug eluting collar 56 is disposed about an exterior of the housing 50 within the distal region 52. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments the distal assembly 42 may include a radiopaque element disposed under the drug eluting collar 56.

The distal assembly 42 includes a coupler 58 that has a distal portion 60 and a proximal portion 62. In some embodiments, the coupler 58 is formed of a metallic material and is configured to move longitudinally and/or rotationally with respect to the housing 50. In some embodiments, as illustrated, the distal portion 60 may have a relatively smaller diameter (relative to the proximal portion 62) in order to accommodate the fixation helix 24. While not illustrated, in some embodiments the proximal portion 62 is configured to accommodate a seal that provides a seal between the coupler 58 and the housing 50.

The fixation helix 24 has a distal region 64 and a proximal region 66. The proximal region 66 of the fixation helix 24 is secured to the distal portion 60 of the coupler 58. One or more attachment methods are used to secure the fixation helix 24 to the coupler 58. In some embodiments, the proximal region 66 of the fixation helix 24 is welded or soldered onto the distal portion 60 of the coupler 58. In some embodiments, the proximal region 66 of the fixation helix 24 has an inner diameter that is less than an outer diameter of the distal portion 60 of the coupler 58, and thus is held in place via compressive forces. In some embodiments the fixation helix 24 is adhesively secured to the distal portion 60 of the coupler 58. In some embodiments, multiple attachment methods are used.

A conductor member 68 has a distal region 70 and a proximal region 72. The distal region 70 of the conductor member 68 is secured to the proximal portion 62 of the coupler 58, and extends proximally through the lead body 22 to the connector assembly 40. The proximal region 72 of the conductor member 68 is coupled to the terminal pin 48 such that rotation of the terminal pin 48 causes the conductor member 68 to rotate.

In some embodiments, the conductor member 68 includes or is otherwise formed from a metallic coil. The coupler 58 provides an electrical connection between the conductor member 68 and the fixation helix 24. In some embodiments, the distal region 70 of the conductor member 68 is welded to the proximal portion 62 of the coupler 58. In some embodiments, the proximal region 72 of the conductor member 68 is welded to the terminal pin 48. The construction of the conductor member 68 can be seen in reference to FIG. 4.

Figure 4:
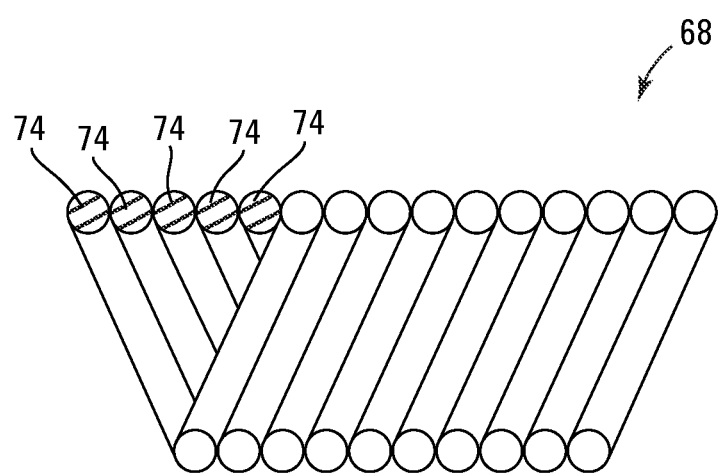
FIG. 4 is a partial cross-section of the lead of FIG. 1

FIG. 4 is a partial cross-section of a portion of the conductor member 68. In some embodiments, as illustrated, the conductor member 68 is formed from a number of individual filars 74 that are arranged next to each other in a ribbon fashion, then collectively coiled to form the conductor member 68. While the conductor member 68 is illustrated in FIG. 4 as having a total of five distinct filars 74, in other embodiments the conductor member 68 can have more or less than five distinct filars 74. In one example, the conductor member 68 may have as many as ten or twelve filars 74. In some embodiments, the conductor member 68 may have only one or two filars 74.

The exact number of filars 74 used to form the conductor member 68 is a matter of choice, and in some cases may be a design issue. In order to provide the lead 14 with a reduced diameter, smaller diameter filars 74 are used. However, to provide a desired level of strength, electrical conductivity and other properties, these small diameter filars 74 can be combined as shown. In some embodiments, the individual filars 74 have a diameter that is in the range of about 0.001 to about 0.002 inches. In some embodiments, the small filar diameters can provide welding complications, particularly when welding the conductor member 68 to a metal structure (such as the coupler 58 or the terminal pin 48) that has a thermal mass that is substantially higher than that of the conductor member 68. In such cases, the individual filars 74 can melt and deform before the larger structure becomes hot enough for high quality welding. Moreover, because the individual filars 74 are quite flexible, there can be difficulties in arranging the individual filars 74 for welding without distorting the individual filars 74.

Returning to FIG. 3, it can be seen that the distal region 70 and the proximal region 72 of the conductor member 68 have been modified. In particular, the distal region 70 includes a first banded portion 76 while the proximal region 72 includes a second banded portion 78. The first banded portion 76 and/or the second banded portion 78 can, in some embodiments, facilitate welding by providing an effectively larger thermal mass. In some embodiments, as illustrated, the first banded portion 76 and/or the second banded portion 78 extends radially around at least a substantial portion of the conductor member 68. In some embodiments, the first banded portion 76 and/or the second banded portion 78 can each include two or more distinct banded region.

Each of the first banded portion 76 and the second banded portion 78 can be formed by subjecting the distal region 70 (or the proximal region 72) to heat and pressure. In some embodiments, heat and pressure can be applied by subjecting a portion of the conductor member 68 to laser energy while applying an axial compressive force to the conductor member 68. In some embodiments, several adjacent filars (or filar turnings) at least partially melt together to form the first banded portion 76 and/or the second banded portion 78. In some embodiments, the first banded portion 76 and/or the second banded portion 78 may each be sized such that they encompass at least as many filars as are used to form the conductor member 68. For example, if the conductor member 68 is formed from a total of 5 individual filars 74, the first banded portion 76 and/or the second banded portion 78 may join together at least 5 adjoining filar turnings.

Once the first banded portion 76 and the second banded portion 78 are formed, the conductor member 68 can be welded to the coupler 58 and the terminal pin 48, respectively, by welding through the first banded portion 76 and the second banded portion 78, Laser welding or resistance welding, in some embodiments, is used to weld the conductor member 68 in place. In some embodiments, as illustrated, a first weld 80 secures the distal region 70 of the conductor member 68 to the coupler 58 and a second weld 82 secures the proximal region 72 of the conductor member 68 to the terminal pin 48.

Once the conductor member 68 is secured to the coupler 58 and the terminal pin 48, rotation of the terminal pin 48 causes the conductor member 68, and hence the coupler 58 and the fixation helix 24, to also rotate. In some embodiments, the fixation helix 24 is rotated via a stylet that is inserted through an aperture that may be formed within the terminal pin 48 (FIG. 2), The lead 14 may include structure that causes the coupler 58 and the fixation helix 24 to translate relative to the housing 50 in response to relative rotation between the coupler 58 and the housing 50.

Any arrangement, whether now known or later developed, for providing the extendable/retractable functionality of the fixation helix 24 can be utilized in connection with the various embodiments of the present invention. In one embodiment, the lead 14 includes structures such as those described and illustrated in co-pending and commonly assigned U.S. Provisional Patent Application 61/181,954, the disclosure of which is incorporated by reference herein in its entirety. In other embodiments, a different arrangement for extending and retracting the fixation helix 24 is utilized.

Figure 5:
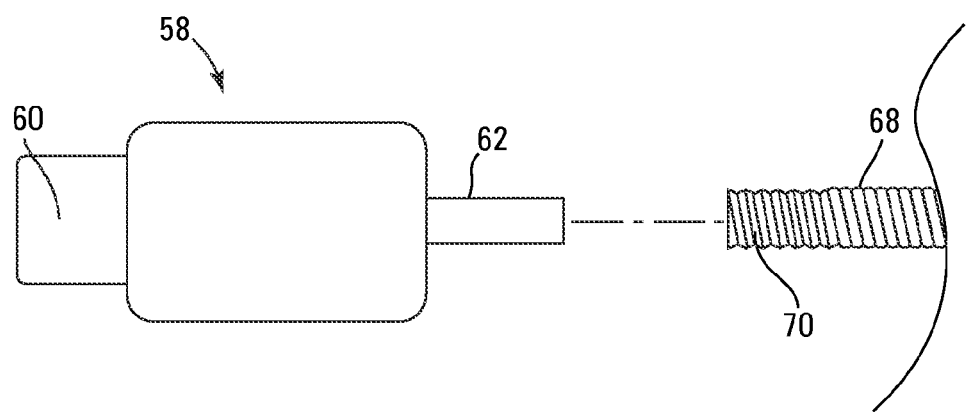
FIG. 5 is an exploded view of an interior portion of the lead of FIG. 1.
Figure 6:
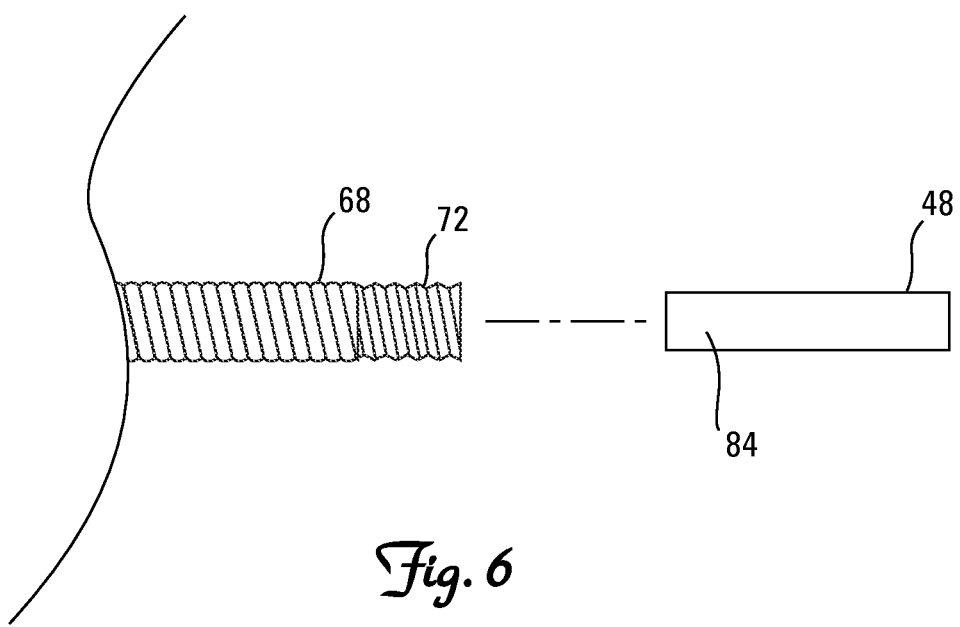
FIG. 6 is an exploded view of an interior portion of the lead of FIG. 1.

FIG. 5 and FIG. 6 provide, respectively, exploded views of the coupler 58 and the terminal pin 48 in combination with a portion of the conductor member 68. In some embodiments, the proximal portion 62 of the coupler 58 is configured to fit within the distal region 70 of the conductor member 68. In some embodiments, the terminal pin 48 has a proximal portion 84 that is configured to fit within the proximal region 72 of the conductor member 68. In some embodiments, the distal region 70 of the conductor member 68 is configured to fit within the proximal portion 62 of the coupler 58. In other embodiments, it is contemplated that a butt joint may be formed between the proximal portion 62 of the coupler 58 and the distal region 70 of the conductor member 68 and/or the proximal portion 84 of the terminal pin 48 and the proximal region 72 of the conductor member 68.

Figure 7:
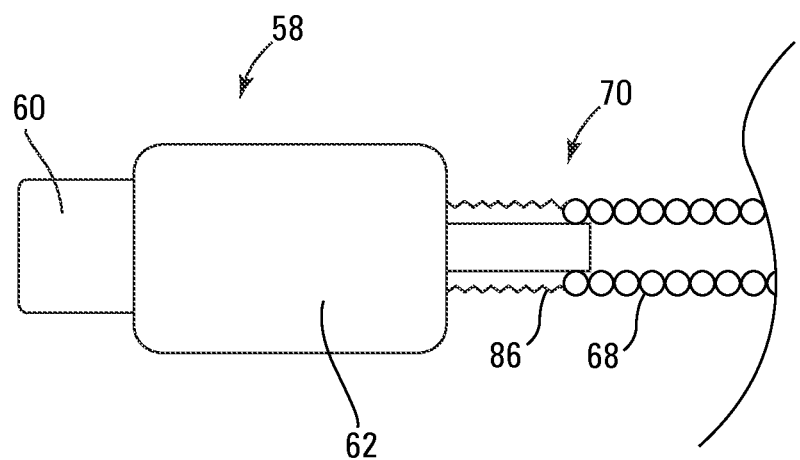
FIG. 7 is an enlarged view of an interior portion of the lead of FIG. 1, showing a conductive member welded to a coupler.

FIG. 7 is an enlarged view of a portion of the lead 14, showing details of the connection between the coupler 58 and the conductor member 68. It can be seen that the distal region 70 of the conductor member 68 includes, in cross section, an at least partially melted and re-solidified portion 86. In some embodiments, the melted and re-solidified portion 86 may be formed using a Nd:YAG laser having a peak power of about 80 watts, a 0.5 millisecond pulse width operating at 10 Hertz and a feed rate of about 0.8 inches per minute.

In some embodiments, as illustrated, the melted and re-solidified portion 86 extends all of the way to a distal end of the conductor member 68. In some embodiments, the melted and re-solidified portion 86 does not extend all of the way to the distal end of the conductor member 68, but is positioned within the conductor member 68 to cover at least a portion of the coupler 58 to facilitate a subsequent welding step.

The melted and re-solidified portion 86 may be considered as forming the first banded portion 76 and can be formed via application of heat and pressure, as discussed above. The melted and re-solidified portion 86 may join together several adjacent filars and may provide a thermal mass sufficient to permit welding therethrough. In some embodiments, three, four, five, six or more adjacent filars can be joined together in forming the melted and re-solidified portion 86. As noted above, the minimum banding width may be selected to include at least as many individual filars as are used to form the conductor member 68. The minimum banding width may be selected to be at least as large as the subsequent weld size. A similar arrangement may be considered between the conductor member 68 and the terminal pin 48.

Figure 8:
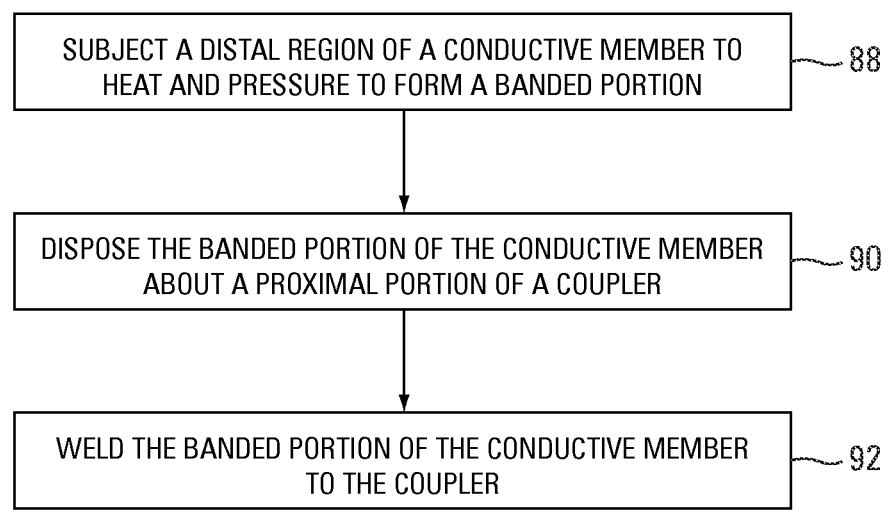
FIG. 8 is a flow diagram showing an illustrative method of assembling the lead of FIG. 1.

FIG. 8 is a flow diagram illustrating a method of assembling the lead 14. A distal region of a conductor member, such as the distal region 70 of the conductor member 68, is subjected to heat and pressure to form a banded portion such as the first banded portion 76, as generally seen at block 88. At block 90, the banded portion is disposed about a proximal portion of a coupler, such as the proximal portion 62 of the coupler 58. Next, the banded portion of the conductive member is welded to the coupler as generally seen at block 92. In some cases, additional assembly steps such as attaching a fixation helix 24 to the coupler 58 to form an assembly, as well as subsequently disposing the assembly within the lead body 22.

Figure 9:
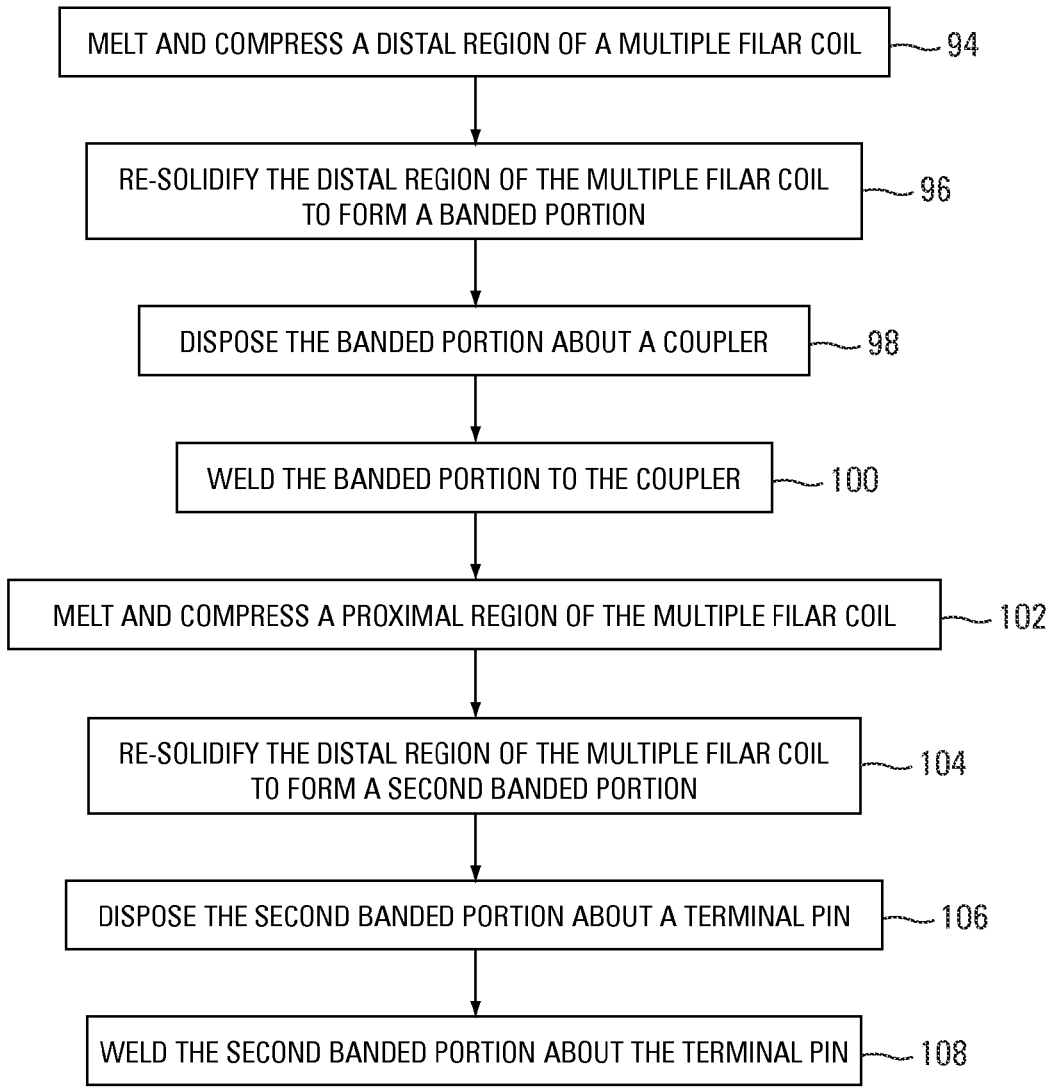
FIG. 9 is a flow diagram showing another illustrative method of assembling the lead of FIG. 1.

FIG. 9 is a flow diagram illustrating a method of assembling the lead 14. A distal region of a multiple filar coil, such as the distal region 70 of the conductor member 68, is melted and compressed, as generally seen at block 94. At block 96, the distal region is re-solidified to form a banded portion such as the first banded portion 76 of the conductive member 68. The banded portion is disposed about a coupler such as the coupler 58, and is then welded to the coupler, as generally seen at blocks 98 and 100.

At block 102, a proximal region of the multiple filar coil is melted and compressed, followed by re-solidifying to form a second band portion such as the second banded portion 78 as shown at block 104. The second banded portion is disposed about a terminal pin such as the terminal pin 48, as generally shown at block 106. At block 108, the second banded portion is welded to the terminal pin.

EXAMPLE

A helical hollow strand (HHS) coil having 12 filars was welded to a metal fitting generically representing a coupler or a terminal pin. The coil tested had a filar diameter of 0.002 inches. In initial tests, coils were separately resistance welded and laser welded to metal fittings with less than desired results.

In subsequent testing, a laser banding process was used to compress, melt and re-solidify adjacent filars prior to welding to the metal fitting. The laser banding process employed a Nd:YAG laser having a peak power of about 80 watts, a 0.5 millisecond pulse width operating at 10 Hertz and a feed rate of about 0.8 inches per minute. A banded HHS coil was then resistance welded to a metal fitting with good results using a Miyachi-unitek weld head equipped with class 13 electrodes, a tip diameter of 0.022 inches, a force of 2 kilograms, a 1 millisecond upslope, a 2 millisecond weld and a 1 millisecond downslope and a welding current of 0.230 kiloamps.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of assembling an extendable/retractable active fixation lead having a coupler and a conductive member secured to the coupler, the conductive member having a distal region and a proximal region, the coupler including a proximal portion configured to accommodate the distal region of the conductive member, the method comprising:
    subjecting the distal region of the conductive member to heat and pressure to form a banded portion;
    disposing the banded portion of the conductive member about the proximal portion of the coupler; and
    welding through the banded portion of the conductive member to secure the coupler to the conductive member.

2. The method of claim 1, wherein subjecting the distal region of the conductive member to heat and pressure comprises subjecting the distal region of the conductive member to laser energy while applying an axial compressive force.

3. The method of claim 1, wherein the conductive member comprises a multiple filar coil.

4. The method of claim 3, wherein subjecting the distal region of the conductive member to heat and pressure comprises banding together a plurality of adjacent filars.

5. The method of claim 4, wherein welding the banded portion to the metal structure comprises welding through the plurality of adjacent filars banded together.

6. The method of claim 1, the lead further comprising a terminal pin, the method further comprising steps of:
    melting and compressing the proximal region of the conductive member;
    re-solidifying the proximal region of the conductive member to form a second banded portion;
    disposing the second banded portion about the terminal pin; and
    welding the second banded portion to the terminal pin.

7. The method of claim 1, further comprising steps of:
    attaching a fixation helix to the coupler to form an assembly; and
    disposing the assembly within a lead body.

8. The method of claim 1, wherein welding through the banded portion to secure the coupler to the conductive member comprises laser welding or resister welding the conductive member to the coupler.

9. A method of assembling an implantable lead comprising a coupler, a terminal pin and a conductive member extending between the coupler and the terminal pin, the conductive member comprising a multiple filar coil having a distal region and a proximal region, the method comprising:
    melting and compressing the distal region of the multiple filar coil and re-solidifying the distal region of the multiple filar coil to form a banded portion;
    disposing the banded portion proximate the coupler;
    welding through the banded portion to secure the coupler to the conductive member;
    melting and compressing the proximal region of the multiple filar coil;
    re-solidifying the proximal region of the multiple filar coil to form a second banded portion;
    disposing the second banded portion proximate the terminal pin; and
    welding through the second banded portion to secure the terminal pin to the conductive member.

10. The method of claim 9, wherein the coupler comprises a shaft portion configured to fit within the distal region of the multiple filar coil, and the method further comprises fitting the distal region of the multiple filar coil over the shaft portion prior to welding the banded portion to the coupler.

11. The method of claim 9, wherein the coupler is configured to accommodate the distal region of the multiple filar coil within the coupler, and the method further comprises fitting the distal region of the multiple filar coil within the coupler prior to welding the coupler to the banded portion.

12. The method of claim 9, wherein the terminal pin is configured to extend within the proximal region of the multiple filar coil, and the method further comprises fitting the proximal region of the multiple filar coil over the terminal pin prior to welding the banded portion to the terminal pin.

13. The method of claim 9, wherein the terminal pin is configured to accommodate the proximal region of the multiple filar coil within the terminal pin, and the method further comprises fitting the proximal region of the multiple filar coil within the terminal pin prior to welding the terminal pin to the banded portion.

14. The method of claim 13, further comprising disposing the coupler and attached conductive member within a lead body.

15. The method of claim 9, wherein welding through the banded portion to secure the coupler to the conductive member comprises laser welding or resister welding the conductive member to the coupler and welding through the second banded portion to secure the terminal pin to the conductive member comprises laser welding or resister welding the conductive member to the terminal pin.

* * * * *